US006429359B1

(12) United States Patent
Lamppa

(10) Patent No.: US 6,429,359 B1
(45) Date of Patent: Aug. 6, 2002

(54) PRODUCTION OF CELLULASE IN PLASTIDS OF TRANSGENIC PLANTS

(75) Inventor: Gayle Lamppa, Chicago, IL (US)

(73) Assignee: ARCH Development Corporation, Chicago, IL (US)

(*) Notice: Subject to any disclaimer, the term of this patent is extended or adjusted under 35 U.S.C. 154(b) by 0 days.

(21) Appl. No.: 09/388,788

(22) Filed: Sep. 2, 1999

(51) Int. Cl.[7] .......................... A01H 5/02; C12N 15/31; C12N 15/62; C12N 15/55; C12N 15/82; C12N 15/56

(52) U.S. Cl. ...................... 800/288; 800/284; 800/278; 800/298; 435/419; 435/320.1; 435/209; 435/69.7; 536/23.4

(58) Field of Search .................. 800/278, 288, 800/298, 284; 435/419, 69.7, 320.1, 209; 536/23.4

(56) References Cited

U.S. PATENT DOCUMENTS

| | | | | |
|---|---|---|---|---|
| 4,940,835 A | * | 7/1990 | Shah et al. | 800/205 |
| 5,712,142 A | * | 1/1998 | Adney et al. | 435/209 |
| 6,013,860 A | * | 1/2000 | Himmel et al. | 800/278 |

FOREIGN PATENT DOCUMENTS

| | | |
|---|---|---|
| WO | WO 96/02551 A1 | 2/1996 |
| WO | WO 98/11235 | 3/1998 |
| WO | WO 98/16651 | 4/1998 |

OTHER PUBLICATIONS

Turk, S. et al. "The vacuolar sorting domain of sporamin transports GUS, but not levansucrase, to the plant vacuole." 1997, New Phytol., vol. 136, pp. 29–38.*

Chaumont, F. et al. "Truncated presequences of mitochondrial F1–ATPase B subunit from Nicotiana plumbaginifolia transport CAT and GUS proteins into mitochondria of transgenic tobacco." 1994, Plant Molecular Biology, vol. 24, pp. 631–641.*

Abad, M.S., et al. (1991) "Soluble Chloroplast Enzyme Cleaves preLHCP Made in *Escherichia coli* to a Mature Form Lacking a Basic N–Terminal Domain." *Plant Physiol* 96: 1220–1227.

Dai, Z., et al. (2000) "Improved Plant–Based Production of E1 Endoglucanase using Potato: Expression Optimization and Tissue Targeting." *Molecular Breeding* 6: 277–285.

Richter, S. and Lamppa, G.K. (1998) "A Chloroplast Processing Enzyme Functions as the General Stromal Processing Peptidase." *Proc. Natl. Acad. Sci. USA* 95: 7463–7468.

Laymon, R.A., et al. (1995) "untitled" Database Embl Sequence Online! (Oct. 10, 1995) accession No. U33212.

Tucker, M.P., et al. (1989) "Ultra–Thermostable Cellulases from *Acidothermus Cellulolyticus*: Comparison of Temperature Optima with Previously Reported Cellulases." *Biotechnology* 7(8): 817–820.

Abad, M., et al. (1988) "Properties of a Chloroplast Enzyme that Cleaves the Chlorophyll a/b Binding Protein Precursor" *Plant Physiol* 90: 117–124.

Richter, S.,et al. (1998) "A Chloroplast Processing Enzyme Functions as the General Stromal Processing Peptidase" *Proc Natl Acad Sci* 95: 7463–7468.

* cited by examiner

*Primary Examiner*—David T. Fox
*Assistant Examiner*—Anne Kubelik
(74) *Attorney, Agent, or Firm*—Alice O. Martin; Barnes & Thornburg

(57) ABSTRACT

A genetic construct encoding a fusion protein including endogluconase E1 and a transit peptide is used to transform plants. The plants produce cellulase by expressing the genetic construct. The cellulase is targeted to plastids and can be collected and purified.

7 Claims, 3 Drawing Sheets

FD+5::E1

FD+15::E1

FD+5::Δ5E1

FD+5::$_{SP10}$E1

FD+5::E1CD

RBCA+5::E1CD

PRODUCTION OF CELLULASE IN PLASTIDS OF TRANSGENIC PLANTS

Figure 1:
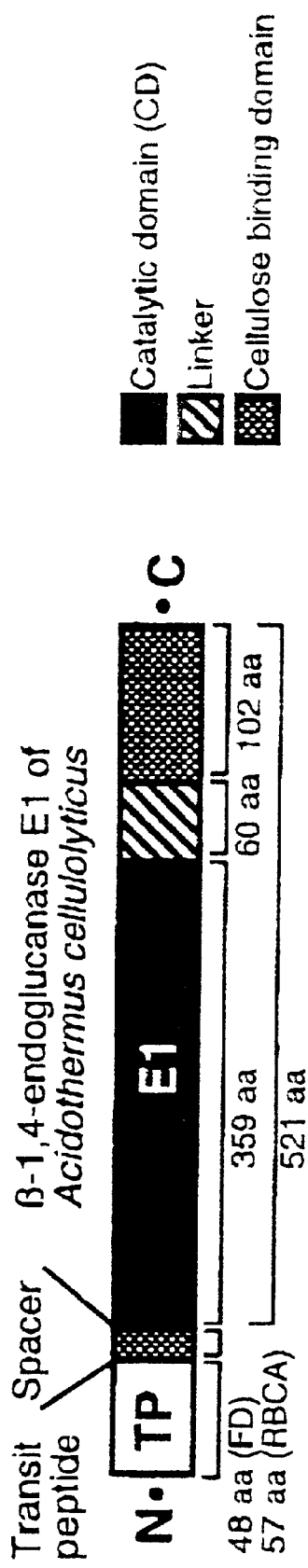

This invention relates to the production of cellulase in plastids using genetic constructs that express a fusion protein including endogluconase E1 fused to a transit peptide. The fusion site is cleavable by a stromal processing peptidase.

BACKGROUND OF THE INVENTION

Cellulose is made up of repeating D-glucose residues, linearly linked via β-1,4-glycosidic bonds. There can be more than 10,000 glucoses per polymer chain. Multiple chains adhere to one another to produce a crystalline structure, which in plant cell walls is usually associated with hemicellulose and lignin producing a complex matrix (Tomme et al., 1995; Teeri, 1997). Cellulose is synthesized by cellulose synthase, an enzyme that has remained elusive in plants until recently when its gene was cloned from Arabidopsis (Arioli et al., 1998).

There are two basic kinds of cellulases required for cellulose degradation. The endocellulases (also called endoglucanases) cleave the polymer chains internally, whereas exocellulases (referred to as exoglucanases) cleave from the reducing and nonreducing ends of the molecule, most often generated by the action endocellulases. Hence, the endo- and exo-cellulases work synergistically, and together are required for degradation of cellulose to glucose and celliogiose. The latter is then further cleaved by β-glucosidase. Hence, a mixture of at least these three enzymes is needed eventually for enzymatic hydrolysis of cellulose for biomass conversion.

Cellulases usually have a structure defined by three domains, although there is considerable variation (Tomme et al., 1995). These include a catalytic domain for glycosidic bond cleavage, a region often rich in proline/serine and threonine that serves as a linker, and a cellulose binding domain (CBD). Endoglucanase E1 from the bacterium *Acidothermus cellulocystis* is useful as a prototype to investigate whether cellulases can be imported into the chloroplast. Endoglucanase E1 was isolated from Yellowstone National Park (Mohagheghi et al., 1986; Tucker et al., 1989). It is a thermostable enzyme, which may favorably affect its recovery in an active form from transgenic plants. It is synthesized as a precursor with a signal peptide that directs it to the export pathway in bacteria. The mature enzyme is 521 amino acids (aa) in length. The crystal structure of the catalytic domain of ~40 kD (358 aa) was recently described (Sakon et al., 1996). Its pro/thr/ser-rich linker is 60 aa, and the CBD is 104 aa. The properties of the CBD that confer its function are not well-characterized. Endoglucanase E1 belongs to family 5 of the cellulases, which is one of the largest classified. These enzymes share a common $(\alpha/\beta)_8$ folded structure with a similar catalytic mechanism, yet they have only 7 conserved residues (Henrissat et al., 1995; Sakon et al., 1996). Mutational analysis shows these are necessary for activity (Bortoli-Terman et al., 1995).

General features of the pathway of protein import into chloroplasts are as follows:. Chloroplasts are multifunctional organelles that carry out numerous important metabolic processes in addition to photosynthesis. They are needed for the synthesis of fatty acids (e.g., palmitic, oleic and linoleic acids), branched (e.g., leucine) and essential aromatic amino acids (phenylalanine, tyrosine, tryptophan), starch, phytohormones, tetrapyroroles, terpenoids, as well as being required for nitrogen and sulfur reduction. Although chloroplasts contain their own transcriptional and translational machineries, only a small fraction of chloroplast proteins are encoded by their own genomes. Instead, the majority of proteins are encoded in the nucleus and synthesized in the cytosol as precursors with an N-terminal transit peptide, which facilities posttranslational import. The pathway of protein import into the chloroplast (and other plastid-types in different tissues) can be divided into six basic steps:

1) precursor polypeptide synthesis in the cytosol,
2) targeting to the envelope,
3) receptor recognition,
4) translocation across the outer and inner membranes,
5) proteolytic processing of the precursor, and
6) folding, localization and assembly of mature proteins within the organelle (a step obviously complicated in itself).

Although an increasingly sophisticated outline of the pathway is emerging, the mechanism underlying each step is not fully understood.

SUMMARY

This invention relates to the production of cellulase in plastids using genetic constructs that express a fusion protein including endogluconase E1 fused to a transit peptide. The fusion site is cleavable by a stromal processing peptidase.

The invention also relates to expression of the gene constructs and production of active endogluconase E1 in vivo and in vitro.

An aspect of the invention is gene constructs that code for a precursor fusion protein with endogluconase E1 fused to a transit peptide, and a site cleavable by a stromal processing peptidase (SPP) at the junction of the transit peptide and endogluconase E1. Endogluconase E1 from *Acidothermus cellulocystis*, a thermophilic bacterium, is sequestered in plastids in an active form. This facilitates the production of usable and relatively inexpensive amounts of cellulase in transgenic plants, which subsequently can be used for cellulose degradation and glucose fermentation to ethanol. Only low levels of cellulase are present in normal plants, compared to transgenic plants made to overexpress the "foreign" or heterologous enzyme using a strong gene promoter.

Plants can serve as storage depots for the overexpression and accumulation of valuable enzymes needed in biotechnology. The enzymes must be accumulated in a site where they will not damage the cell. In the present invention, large amounts of the cellulase are sequestered away from the cell wall itself, where the enzyme might cause a modified or defective phenotype. Furthermore, there are hundreds of plastids (chloroplasts) per cell available to accumulate large amounts of cellulase. Therefore, the chloroplasts may also be isolated to enrich production.

Sequestering of endogluconase E1 in plastids in an active form may be the best approach to produce cellulase in transgenic plants. An aspect of the invention is to generate large amounts of this enzyme by recombinant technology for the degradation of cellulose to fermentable sugars, eventually yielding ethanol as an alternative fuel to fossil fuels.

To successfully express and import β-1,4-endoglucanase E1 peptide (E1) into the stroma of plants, special gene constructs needed to be created. Constructs that code for a precursor fusion protein with E1 fused to a transit peptide and a site cleavable by the stromal processing peptidase (SPP) were developed.

Transit peptides and passenger proteins (the proteins transported by the transit proteins) must not fold or aggregate into structures that interfere with efficient processing and import for embodiments of the present invention. That is, they should be compatible. To obtain these fusion proteins, E1 and its catalytic domain (E1CD) were fused to two different transit peptides (TP). Both TP used, ferredoxin (FD) and Rubisco activase (RCBA), were linked to the E1 (521 amino acids in length) and E1CD (359 amino acids in length) passenger proteins. This alteration of the fused protein changed the efficiency by which cleavage and importation of the fused peptide occurred. To further study the efficiency of proteolytic processing and import, the number of amino acids in a spacer region immediately following the cleavage site (between the TP and passenger protein) was altered. Constructs that were developed were fused via a spacer region of 1, 5, 10, or 15 amino acid residues. The spacer region is between the cleavage site and the beginning of the E1 amino acid sequence.

One particular array of fusion proteins was made using the transit peptide of ferredoxin (FD). An unexpected finding was that the efficiency of proteolytic processing and import was significantly affected by the number of amino acids immediately following the cleavage site, before the start of the E1 amino acid sequence. Therefore, it appears that the spacing at the transit peptide-E1 junction is critical. This conclusion is supported by the observation that an insertion after the cleavage site of the C-terminal 10 amino acids from the signal peptide of E1 which is normally synthesized as a precursor that is exported from Acidothermus—also promotes processing and import.

Another unexpected finding is that a fusion protein containing only the catalytic domain (CD) of E1 is more readily cleaved and imported than a comparable precursor with full length E1. Both the E1 and CD polypeptides are enzymatically active when synthesized in vitro.

Extending the results with the transit peptide of FD, the transit peptide of Rubisco activase (RBCA) was fused to E1 and to CD. In comparable constructs, each transit peptide conferred different properties. Nevertheless, precursors with the transit peptide of RBCA were also cleaved by SPP and imported into chloroplasts.

An aspect of the invention is a fusion protein that includes endogluconase E1 and a transit peptide. The endogluconase E1 and transit peptide are joined to form a junction site that is cleavable by a stromal processing peptidase (SPP) discovered by the inventors and originally designated "CPE" (chloroplast processing enzyme) before its ability to cleave most precursors targeted to the chloroplast was established. Suitable transit peptides include the peptide that transports ferredoxin (FD) and the peptide that transports Rubisco activase (RBCA). The fusion protein may include only a part of endoglucanase E1, preferably the catalytic domain (CD).

Another aspect of the invention includes a plant transformed with a fusion protein of the present invention.

Another aspect of the invention includes a method of producing cellulase in the plastids of transgenic plants. The method includes the following steps:

(a) expressing active endogluconase E1 in the transgenic plant; and (b) collecting cellulase made by the transgenic plant.

Other aspects are a genetic construct comprising cDNA encoding a fusion protein of the present invention. The nucleus contains the gene construct. The chloroplasts will contain active E1 enzyme, without a transit peptide,

BRIEF DESCRIPTION OF THE DRAWINGS

FIG. 1 shows a schematic representation of genetic expression constructs for accumulation of E1 in chloroplasts, (abbreviations: aa, amino acid; FD, ferredoxin; RBCA, Rubisco activase).

FIG. 2 shows representative examples of constructs of the present invention processed by recombinant stromal processing peptidase (SPP) (Richter and Lamppa, 1998) and a chloroplast extract from pea; (Abad, et al. 1989) processed samples were analyzed with SDS-PAGE gel; lane 1 of each contains untreated [$^{35}$S]methionine-labeled precursor fusion proteins as a control, lane 2 contains precursor proteins processed with recombinant SPP, and lane 3 contains precursor protein processed with chloroplast extract from pea. Abbreviations: p, precursor (fused protein); m, mature E1 or E1CD.

FIG. 3 indicates in vitro chloroplast import of representative E1 precursor fusion proteins. Abbreviations: T, 1 $\mu$l translation product; S and M, stromal and membrane fraction, respectively; p, E1 fusion precursor; m, mature E1 or E1CD.

DETAILED DESCRIPTION OF THE INVENTION

Successful accumulation of active cellulase in the chloroplasts of transgenic plants is a useful accomplishment because cost of production of cellulase is decreased and there is increased ease of production. Expression of the E1 gene in the nucleus may allow for specific control and regulation, as well. Endogluconase E1 from *Acidothermus cellulocystis*, a thermophilic bacterium (obtained from Steven Thomas, NREL), was selected to enhance cellulase production in plastids. That is, expression of E1 is temperature-dependent and thus can be prevented until temperatures are elevated. Precursor fusion proteins with signals that specifically target E1 to the chloroplast were synthesized. In the chloroplast, the signal—called the transit peptide—was then cleaved, releasing mature E1 within the organelle (i.e., the plastid). Fusion proteins were tested in vitro for proteolytic processing and import into isolated chloroplasts in order to select the best candidates for more costly in vivo studies using transgenic plants. The junction between the transit peptide and E1 was found to be a critical region within the structure of the precursor. In addition, different transit peptides affect processing and import to different degrees.

Active E1 was expressed in an in vitro system starting with the E1 gene. Expression includes in vitro transcription followed by in vitro protein synthesis. Surprisingly, an active enzyme was obtained. This allowed in vitro studies to explore the import and release of active E1 in the chloroplast. Many constructs were synthesized. A standard polymerase chain reaction known to those of skill in the art was used to generate fragments for cloning. Further, E1 structure may be genetically manipulated and used to test how changes in structure influence its activity. Many predictions have been made based on structural analyses and evolutionary comparisons of cellulases that can be tested using the in vitro expression system, which should facilitate a comprehensive study on structure-function relationships.

Several important and useful genetic constructs encoding precursor fusion proteins that are efficiently cleaved and imported into chloroplasts in vitro were identified. See Table 1 for specific characterizations. Samples are incubated with pea chloroplast and then stromal and membrane fractions of chloroplast (with or without thermolysin treatment as indicated by −/+), are separated and analyzed by SDS-page. Results are included in Table 1.

Five genetic constructs were selected for transformation of tobacco. The genes were placed downstream of the nearly constitutive CaMV 35S promoter with 5' and 3' nontranslated regions as part of a cassette. This promoter is usually active at high levels, with little variation between tissues. The selection of this promoter was made to assure fairly high transcription levels. Leaf disks were inoculated with Agrobacterium and plants regenerated by procedures well known to those of skill in the art, were analyzed within 4–6 weeks after inoculation. The level of E1 and endogluconase activity are examined in different tissues of the transgenic plants, beginning with leaves. Total cellular protein levels are assayed. Plastids are isolated to determine the success of targeting E1 to the chloroplast. An active endogluconase was recovered by in vitro translation. That the transit peptide affects this activity is based on in vitro experiments. See Table 2.

As more complicated constructs were made, it was realized that the addition or deletion of amino acids at the N-terminus of E1 might influence endoglucanase activity. Therefore, there was good reason to attempt in vitro expression. Furthermore, there was a possibility of manipulating cellulase activity genetically if a relatively rapid assay was available for analyzing mutant constructs. These experiments were successful. Active E1 as well as its CD was synthesized by in vitro transcription of their respective genes followed by translation of their transcripts. Unexpectedly, the precursor fusion proteins were active. Activity is inhibited by a specific mutation at the N-terminus of E1 in the precursor, and optimal activity depends on high temperature. Studies on the import of E1 and its CD into isolated chloroplasts, using the array of constructs already created are extended to include assays for a functional enzyme after transport into the organelle in vitro.

A series of fusion proteins were synthesized and analyzed. Importantly, they demonstrate the specificity of SPP's recognition of different substrates. (See Table 1.) Analysis of E1 expression in transgenic tobacco is made after the original lines are crossed made homozygous for the "transgene." Seed from these transgenic plants are useful for further detailed biochemical studies, specifically assaying for cellulase activity.

EXAMPLES

The following examples are embodiments of the present invention.

Example 1

Genetic constructs were made that code for a precursor fusion protein with endogluconase E1 fused to a transit peptide and a site cleavable by the stromal processing peptidase (SPP) at the junction.
A. Precursor fusion proteins using the ferredoxin transit peptide.
  1. Constructs using full-length endogluconase E1 with insertions or a specific deletion.
A series of constructs were designed that encoded precursor fusion proteins with E1 linked to the transit peptide of ferredoxin (FD). The FD transit peptide is considered to possess considerable structural flexibility, and has been used previously to import some proteins into chloroplasts (de Boer et al., 1991; Pilon et al., 1992). Table 1 lists each construct (#1–#11) used and shows the structure at the transit peptide-to-mature protein junction of each precursor fusion protein. Results from assays are also tabulated in Table 1. The relative amount of precursor processed is as follows: >75%, +++; 75–25%, ++; <25%, +.

In the first three precursors, the transit peptide and cleavage site were left intact and an increasing number of amino acids—one, five and fifteen residues—from mature ferredoxin were included as a spacer before the start of mature E1.

To determine the efficiency of each construct that was created, each precursor fusion protein was labeled with [$^{35}$S]methionine and was processed in vitro by recombinant SPP from *E. coli* bacteria and a chloroplast extract from pea. (Richter and Lamppa, 1998).

Figure 2:
Figure 2:
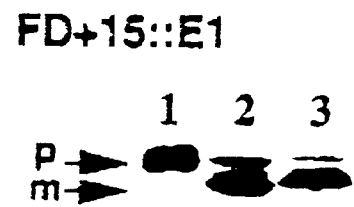
Figure 2:
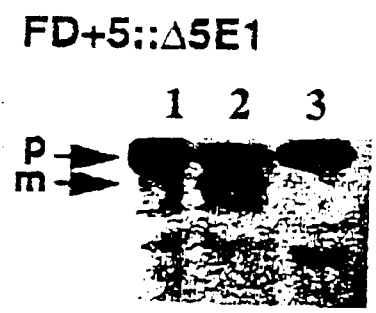
Figure 2:
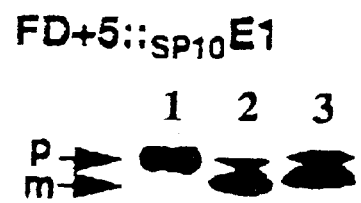
Figure 2:
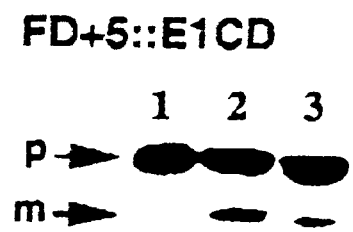
Figure 2:
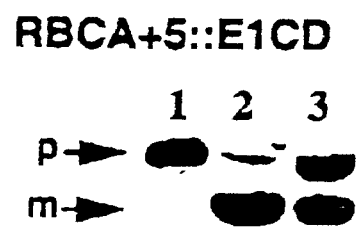

To analyze the samples following incubation, SDS-PAGE gels were run and stained for protein fragments. Processed precursors that produced fragment samples with a molecular weight for the mature protein of ~56KD (or 56,000D) indicated that E1 protein cleavage did occur and that it occurred near the correct location. The relative amounts of precursor that were processed were assessed by comparing band signal densities using a PhosphoImager and are listed in Tables 1 and 2. FIG. 2 depicts representative samples of gels containing the SPP and chloroplast extracted treated constructs.

Relative activity was examined by hydrolysis of the substrate 4-methylumbelliferyl β-D-cellobioside (MUC) which liberates the fluorescent product 4-methylumbelliferone (MU). All constructs were under T7 bacteriophage promoter control and were expressed in coupled transcription/translation reactions (50 μl standard reactions, TNT System, Promega). Translation product (5 μl) was added to 200 μl 0.5 mM MUC in reaction buffer (100 mM sodium chloride, 50 mM sodium acetate, pH5) and incubated at 65° C. or 37° C. for 30 minutes. To stop a reaction, 200 μl of 150 mM glycine-NaOH; pH 10 were added. The relative amount of released MU was measured as fluorescence using 365 nm excitation and 456 nm emission filters. All translation products were also radio-labeled using [$^{35}$S]methionine in TNT standard reactions and quantified upon SDS-PAGE. A specific factor was calculated for each E1 construct and used to normalized fluorescence values.

Figure 3:
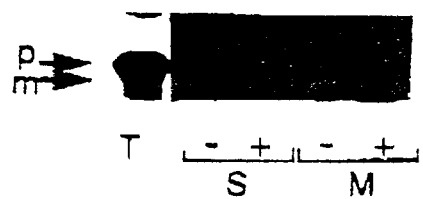
Figure 3:
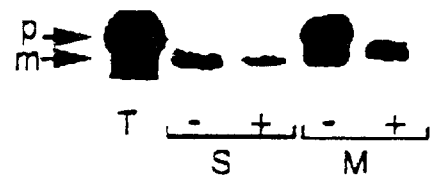
Figure 3:
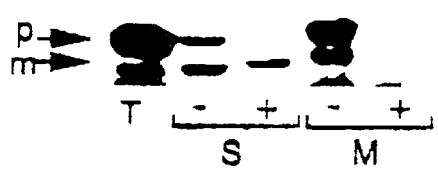
Figure 3:
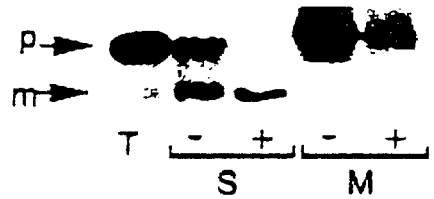

To study the degree of in vitro chloroplast import of E1 precursor fusion proteins, radiolabeled [$^{35}$S]methionine precursors were incubated with pea chloroplasts for 20 minutes. Samples were then incubated with stromal and membrane fractions of chloroplasts with or without thermolysin treatment (indicated as −/+) and were separated and analyzed by SDS-PAGE gel (Lamppa, 1995). FIG. 3 illustrates representative data from the SDS-PAGE gels and Table 1 characterizes import and activity status of each construct.

Construct #2 (FD+1::E1, ferredoxin transit peptide plus one amino acid from mature FD fused to E1 transit peptide plus one amino acid fused to E1) was not proteolytically cleaved by recombinant SPP from *E. coli* or by a soluble chloroplast extract. Construct #3 (FD+5; E1) was cleaved very weakly by SPP, and not at all by the chloroplast extract (FIG. 2). Neither construct was imported into chloroplasts isolated from pea. On the other hand, an increase in the spacer region to 15 residues in construct #4 (FD+15::E1) yielded a precursor that was efficiently cleaved by SPP and the chloroplast extract (FIG. 2). Furthermore, FD+15::E1 was imported into the chloroplast, processed, and most of mature E1 was found in the stromal fraction (FIG. 3). Thermolysin treatment of the chloroplasts demonstrated that E1 was indeed sequestered within the organelle.

Construct #2 was not processed, construct #3 was processed inefficiently, and, further, neither were imported. Consequently, whether the unusual residues at the start of E1—Ala-Gly-Gly-Gly-Tyr (AGGGY)—(SEQ ID NO: 1) might prevent (or compromise) recognition of the transit peptide by SPP and the chloroplast import machinery was considered. Glycines are well-known to alter protein conformation. Therefore, in construct #5 (FD+5::Δ5E1) these residues were deleted. Although FD+5::E1 itself was not efficiently processed or imported, the AGGGY (SEQ ID NO: 1) deletion resulted in a precursor that was cleaved by SPP. However, the chloroplast extract did not remove the transit peptide. (One explanation for the discrepancy is that recombinant SPP is significantly more "robust" than SPP in the chloroplast extract, and there is thus a difference between the amount of active SPP relative to the substrate.) FD+5::Δ5E1 was also imported into chloroplasts, and cleaved. It is likely that the very N-terminal AGGGY (SEQ ID NO: 1) of E1 can have a negative effect on different steps in the import pathway if located in close proximity to the transit peptide.

To test whether a spacer was needed between the transit peptide and E1 for efficient cleavage, as suggested from results with construct #4 (FD+15::E1), construct #6 (FD+5::sp10E1) was generated containing the 5 residues from mature FD and an additional 10 amino acids from E1's own signal peptide. The introduction of this spacer sequence yielded a precursor that was efficiently cleaved by SPP and the chloroplast extract. It was also imported into the chloroplast, processed and 40% was found in the stroma and 60% in the membrane fraction after thermolysin treatment. That sp10E1 is found in the membrane fraction is probably due to the presence of the region from the signal peptide, which contains a number of hydrophobic residues (Ala, Val, and Pro).

2. Constructs using the catalytic (CD) domain of E1.

E1 is comprised of three domains: the N-terminal catalytic domain (CD), the serine-proline rich linker, and the C-terminal cellulose binding domain (CB), as illustrated in FIG. 1. Other structural features of E1—in addition to the AGGGY sequence—(SEQ ID NO: 1) were in some way affecting processing by SPP and transport into the chloroplast. To investigate whether CD alone—separated from the linker and CB—fused to a transit peptide would be a better substrate in these reactions, three new precursor fusion proteins were synthesized: construct #7 (FD+1::E1CD, i.e. FD transit peptide plus 1 amino acid fused to CD); construct #8 (FD+5::E1CD); and construct #9 (FD+5::Δ5E1CD).

When only one amino acid followed the transit peptide in construct #7 (FD+1::E1CD), the precursor was not processed by SPP. In contrast, both construct #8 (FD+5::E1CD, FIG. 2) and construct #9 (FD+5::@5E1CD) were processed, albeit not as well as several other constructs listed in Table 1. Import was quite efficient for both precursors. The results for FD+5::E1CD are shown in FIG. 3.

B. Precursor fusion proteins using the transit peptide of Rubisco activase.

Transit peptides do not share a common primary sequence. Therefore, to determine if an alternative to the FD transit peptide would yield a precursor containing E1 that was more efficiently recognized in the processing and import assays, ribulose-bisphosphate carboxylase/oxygenase activase (RBCA) was selected because it was found previously that, at least in vitro, the RBCA precursor itself is very efficiently cleaved by SPP. Two constructs were made with the RBCA transit peptide plus five amino acids from mature RBCA: construct #10 (RBCA+5::E1), and construct #11 (RBCA+5::E1CD).

Construct #10 (RBCA+5::E1) was cleaved by SPP from E. coli, but not by the chloroplast extract. A possibility is that features of some substrates are not recognized by SPP in the context of other factors in the chloroplast extract. However, RBCA+5::E1 was imported and cleaved. Construct #11 (RBCA+5::E1CD) contained the CD fused to the transit peptide, and it was processed very efficiently (FIG. 2) and imported (FIG. 3). From a comparison of the results using the RBCA+5 constructs (#10 and #11) versus the FD+5 constructs (#3 and #8), it was concluded that RBCA+5 promotes more efficient processing of the E1 precursors by SPP. A careful quantitation of the import reactions may be performed for comparison with a subset of precursor fusion proteins, knowing which are efficiently cleaved by SPP and where import reactions have been successful. A goal is to find the best construct for efficient translocation and accumulation of active E1 in the plastid.

Example 2

Expression of genetic constructs and production of endogluconase E1 in vivo.

The basic expression cassette disclosed herein was used for transformation of tobacco (Table 1, far left column, lists the different constructs introduced into tobacco). Tobacco disks were transformed and shoots developed on numerous calli growing from leaf disks. The FD transit peptide::E1 constructs (#4, #6 and #8) that were positive in the in vitro processing and import assays, were selected as well as construct #3 that was negative. The latter might generate an interesting phenotype for comparison if E1 is localized to the cytoplasm. In addition, construct #1; that is, E1 without a transit peptide, was included.

Based on results with the RBCA transit peptide constructs, construct #11 containing the catalytic domain of E1 is also suitable to introduce into tobacco. Transgenic plants are developed before developing new constructs, because of the large number of individuals that must be examined for a thorough analysis and accurate interpretation of what happens to E1 expression in vivo.

Example 3

An active endogluconase recovered by in vitro translation, and effects of the transit peptide on activity.

Expression of E1 was determined in an active form following in vitro transcription and translation. Nine of the constructs shown in FIG. 1 were tested, and results are presented in Table 1. Each one of these genes was inserted downstream of the T7 bacteriophage promoter, allowing for in vitro transcription and coupled translation in a TNT system (Promega). This system includes a reticulocyte lysate for synthesis of radiolabeled protein. The activity of the translation products was monitored using a MUC assay that is very similar to a β-glucuronidase (GUS) assay. Experiments were first carried out at 65° C. and fluorescence was measured. Table 2 demonstrates that the values obtained are within the linear range of detection. Units of fluorescence were proportional to concentration of the product yield, and values fell within this linear range.

Significantly, active E1 was synthesized in the in vitro expression system. Unexpectedly, however, six of the precursor fusion proteins exhibited nearly as much activity as endogluconase E1 without a transit peptide. Construct #3 (FD+5::E1) showed 85% of the activity found for E1 alone, and construct #10 (RBCA+5::E1) showed 93% of E1 activity. Precursors with only the catalytic domain of E1 were also tested. Construct #8 (FD+5; E1CD) contained 67% activity compared to E1. On the other hand, construct #11 (RBCA+5::E1CD) was significantly more active—showing 126% of E1 activity.

The two precursors—constructs #5 and #9—with the AGGGY (SEQ ID NO: 1) deletion near the N-terminus of E1 showed a very low level of activity (9% and 11% of E1 activity, respectively), yet for both it was reproducibly higher than the control reactions, where a background of 2% activity was found using a vector containing the gene for the native precursor of RBCA (without the E1 coding region), or no vector at all in the MUC assay.

The MUC reactions were performed at 65° C. again; only, for these lists the precursor fusion proteins with recombinant SPP were treated first (see Table 1, legend) There was an average of ~21% increase in endogluconase activity after processing by SPP (Table 1). These results show that the transit peptide can function as a separate domain from the mature protein, and does not dramatically interfere with the enzymatic activity of E1 under these in vitro conditions and in this particular assay. However, transit peptide removal yields a more active E1 cellulase. Conditions may also exist where the transit peptide has a more inhibitory effect on the ability of E1 to carry out its role in cellulose degradation. Further, it might be crucial that transit peptide removal is accomplished within the organelle after import, since proteins with transit peptides may be a target for degradation, or interfere with organelle biogenesis if accumulated.

Next, MUC assays were carried out at 37° C. for a subset of the constructs. Since E1 is from a thermophilic bacterium, the native enzyme is most active at elevated temperatures. Indeed, about a 50% drop in endogluconase activity in the MUC assay was found at the lower temperature compared to 65° C. The temperature optimum for the E1 synthesized in vitro may be determined by repeating the experiments at a range of temperatures.

The reaction carried out by E1 expressed in the in vitro eukaryotic (reticulocyte lysate) system is specific for demonstrating cellulase activity using a fluorescent assay as described in Table 2.

Example 4

Production of cellulase by transgenic plants

A gene encoding endogluconase E1 was introduced into an expression vector downstream of a bacteriophage promoter for in vitro expression. mRNA was translated in vitro using a reticulocyte lysate. Genetic constructs were tested both for proteolytic processing and removal of the targeting signal (transit peptide) and for import into chloroplasts isolated from pea. Because results were positive, this construct was used in transformation of tobacco for the transgenic analysis. See FIG. 1 for transformants.

MATERIALS AND METHODS

Transformation Protocol for the Production of Transgenic E1 Tobacco Plants

The protocol is now a standard leaf disk assay developed over a period of 10 years by different groups.

1. Make multiple cuts (longitudinal incisions) on whole leaves from in vitro tobacco plants grown in culture. Inoculate freshly cut leaves with Agrobacterium cells for 10 mm.
2. Cocultivate infected leaves with Agrobacterium on MS medium for 3 days.
3. Transfer leaves to MS shooting medium with 500 mg/L cefotaxime and 200 mg/L kanamycin for elimination of bacteria and regeneration of transgenic shoots. Resistant calli and shoots appeared in 3–4 weeks after selection started.
4. Excise shoots from calli and root then in a rooting medium containing 0.025 mg/L NAA and 250 mg/L cefotaxime and 200 mg/L kanamycin.
5. Pot kanamycin resistant transgenic plants in soil. Transfer to greenhouse.

The above protocol was modified from Fisher and Guiltinan (1995).

TABLE 2

Fusion Protein Construct Structure and Characterizations Assays: (a) Proteolytic processing, (b) Transport into isolated chloroplasts, (c) enzyme activity and (d) initial transgenic plants

| Gene Construct Coding for Protein Construct (Fusion Protein.) | Transit Peptide-E1 Junction | (a) Proteolytic Processing | | (b) Transport into Isolated Chloroplasts | (c) Measure of Cellulase Activity | (d) Transgene Started |
|---|---|---|---|---|---|---|
| | | SPP[1] | Extr.[2] | | | |
| 1 E1 | M AGGGYW- | N.D.* | N.D.* | N.D.* | Yes | Yes |
| 2 FD+1::E1 | -RVTAM A................AGGGYW- | − | − | No | N.D.* | No |
| 3 FD+5::E1 | -RVTAM ATYKV............AGGGYW- | I | I | No | Yes | Yes |
| 4 FD+15::E1 | -RVTAM ATYKVTLITKESGTV...AGGGYW- | +++ | +++ | Yes | Yes | Yes |
| 5 FD+5::Δ5E1 | -RVTAM ATYKV ...................W- | ++ | ++ | Yes | No | No |
| 6 FD+5::$_{SP10}$E1[3] | -RVTAM ATYKV ............AGGGYW- | +++ | +++ | Yes | Yes | Yes |
| 7 FD+1::E1CD | -RVTAM A ................AGGGYW- | − | − | N.D.* | N.D.* | No |
| 8 FD+5::E1CD | -RVTAM ATYKV............AGGGYW- | ++ | ++ | Yes | Yes | Yes |
| 9 FD+5::Δ5E1CD | -RVTAM ATYKV..................W- | ++ | ++ | Yes | No | No |
| 10 RBCA+5::E1 | -SMTVK AAENE............AGGGYW- | ++ | ++ | Yes | Yes | No |
| 11 RBCA+5::E1CD | -SMTVK AAENE............AGGGYW- | +++ | +++ | Yes | Yes | No |
| | Transit Spacer[4] E1 Peptide | | | | | |

[1]Recombinant SPP;
[2]Chloroplast extract;
[3]SP10:10 aa of C-terminus of E1 signal peptide;
[4]N-terminus of mature FD or RBCA
*N.D.= Not determined. Abbreviations: aa= amino acid; FD= ferredoxin; RBCA= Rubisco activase.
Amino acids
R= arg
V= val
T= thr
A= ala
M= met
Y= tyr
K= lys
G= gly
W= trp
S= ser

TABLE 2

Relative activities of E1 expression constructs in vitro

| | Relative amount of released MU | | | | | |
|---|---|---|---|---|---|---|
| | at 65° C. | | at 65° C. SPP Processing[1] | | at 37° C. | |
| Constructs | Units[2] | %[3] | Units[2] | %[3] | Units[2] | %[4] |
| 1 E1 | 54.98 ± 0.34 | 100 | | | 25.14 ± 0.59 | 46 |
| 3 FD + 5::E1 | 46.76 ± 0.73 | 85 | 57.53 ± 0.61 | 105 | 22.36 ± 0.41 | 48 |
| 4 FD + 15::E1 | 41.60 ± 0.62 | 76 | 54.66 ± 1.36 | 99 | | |
| 6 FD + 5::$_{SP10}$E1 | 6.30 ± 0.82 | 11 | 7.34 ± 0.08 | 13 | | |
| 8 FD + 5:E1CD | 37.00 ± 0.16 | 67 | 41.92 ± 0.69 | 76 | 15.37 ± 0.20 | 41 |
| 9 FD + 5::66 5E1 | 5.22 ± 0.14 | 9 | 11.38 ± 0.30 | 21 | | |
| 10 RBCA + 5::E1 | 51.13 ± 0.41 | 93 | 65.48 ± 0.34 | 119 | 23.50 ± 0.39 | 36 |
| 11 RBCA + 5::E1CD | 69.06 ± 0.45 | 126 | 83.64 ± 0.28 | 152 | 24.75 ± 0.28 | 30 |
| PreRBCA | 1.00 ± 0.09 | 2 | | | | |
| Control[5] | 1.07 ± 0.10 | 2 | | | | |

[1]Translation products were processed by recombinant SPP before MUC assay (Richter and Lamppa, 1998, PNAS 95: 7463–7468).
[2]Fluorescence units, means of five measurements
[3]Relative amount of MU released by E1 was taken as 100%.
[4]Relative amount of MU released at 65° C. was taken as 100%.
[5]Master mix of TNT System.

TABLE 3

MU standard

| [MU] in nM | Units[1] |
|---|---|
| 40.0 | 156.74 ± 1.70 |
| 16.0 | 62.31 ± 0.53 |
| 8.0 | 30.37 ± 0.30 |
| 4.0 | 15.15 ± 0.16 |
| 2.0 | 7.73 ± 0.18 |
| 1.0 | 3.91 ± 0.12 |
| 0.5 | 2.08 ± 0.13 |
| 0.25 | 1.02 ± 0.07 |
| 0.125 | 0.56 ± 0.05 |

[1]Fluorescence units, means of five measurements

DOCUMENTS CITED

Abad, M., Clark S. and Lamppa, G. (1988) Properties of a chloroplast enzyme that cleaves the chlorophyll a/b binding protein precursor. *Plant Physiol.* 90: 117–124.

Arioli, T., Peng, L., Betzner, A., Bum, J., Wittke, W., Herth, W., Camilleri, C., Hofte, H., Plazinski, J., Brich, R., Cork, A., Glower, J., Rdmond, J. and Williamson, R. (1998) Molecular analysis of cellulose biosynthesis in Arabidopsis. *Science* 279: 717–719.

Bortoli-Terman, I., Haiech, J., Chippauz, M. and Barras, F. Information suppression to investigate structural, functional and evolutionary aspects of Ervinia chrysanthemi cellulase EGZ. *J. Mol. Biol.* 246: 82–94.

DATABASE Locus ACU33212 ACCESSION # U33212, from the organism *Acidothermus cellulyticus*.

de Boer et al. (1991) *EMBO J.* 10: 2765–2772.

Fisher, D. K and Guiltinan, M. K, (1995). *Plant Mol. Biol. Reporter.* 13(3):278–289.

Henrissat, B., Callebaut, I., Fabrega, S., Lehn, P., Moron, J-P. and Davies, G. (1995) Conserved catalytic machinery and the prediction of a common fold for several families of glycosyl hycdrolases. *Proc. Natl. Acad. Sci.* 92: 7090–7094.

Lamppa, (1995). *Meth. Plant Mol. Biol.* 141–171.

Mohagheghi, A., Grohmann, K., Himmel, M., Leighton, L. and Uptedegraff, D. (1986) Isolation and characterization of Acidothermus celluloyticus, a new genus of terhmophilic, acidophilic cellulolytic bacteria. *Int. J. System. Baceriol.* 36: 435–443.

Pilon, M., Wienk, H., Sips, W., deSwaff, M. Talboom, I. van't Hof, R., de Korte-Kool., G., Demel., R., Weisbeek, P., and de Kruijff, B. (1995) Functional domains of ferredoxin transit sequence involved in chloroplast import. *J. Biol. Chem.* 270: 3882–3893.

Richter and Lamppa, (1998) *PNAS* 95: 7463–7468.

Sakon, J., Adney, W., Himmel, M., Thomas, S. and Karplus, P. (1996). Crystal structure of thermostable family 5 endocellulase E1 from Acidothermus cellulolyticus in complex with cellotetraose. *Biochem.* 35: 10648–10660.

Teeri, T. (1997). Crystalline cellulose degradation: new insight into the function of cellobiohydrolases. *TIBTECH* 15: 160–167.

Tomme, P., Warren, R. and Gilkes, N. (1995) Cellulose hydrolysis by bacteria and fuingi. *Adv. Micro. Physiol.* 37: 1–80.

Tucker et al. (1989). *Biotechnology* 7: 817–820.

I claim:

1. A plant transformed with a genetic construct encoding a fusion protein comprising endogluconase E1 and an RBCA transit peptide capable of tansporting the fusion protein to cihoroplasts, wherein said endogluconase E1 and said BCA transit peptide are joined to form a junction site that is cleavable by a stromal processing peptidase (SPP), and are separated by a peptide acid spacer, and wherein said genetic construct is expressed as protein, which is stored in chloroplasts of the transformed plant.

2. A genetic construct comprising a cDNA encoding a fusion protein comprising a catalytic domain of endogluconase E1 and a transit peptide capable of transporting the protein into chloroplasts, wherein said catalytic domain of endogluconase E1 and said transit peptide are joined to form a junction site that is cleavable by a stromal processing peptidase and are separated by at least a 5 amino acid long spacer.

3. The genetic construct of claim 2, wherein the 5 amino acid spacer has the amino acid sequence of the first 5 amino acids of any mature chloroplast protein.

4. A plant transformed with a genetic construct encoding a fusion protein comprising a catalytic domain of endogluconase E1 and an RBCA transit peptide capable of transporting the fusion protein to chloroplasts, wherein said catalytic domain of endogluconase E1 and said RBCA transit peptide are joined to form a junction site that is cleavable by a stromal processing peptidase (SPP), and are separated by a peptide spacer, and wherein said genetic construct is expressed as protein which is stored in chloroplasts of the transformed plant.

5. A genetic construct encoding a fusion protein comprising endogluconase E1 and an RBCA transit peptide capable of transporting the fusion protein to chloroplasts, wherein said endogluconase E1 and said RBCA transit peptide are joined to form a junction site that is cleavable by a stromal processing peptidase (SPP), and are separated by a peptide spacer.

6. A plant transformed with a genetic construct comprising a cDNA encoding a fusion protein comprising a catalytic domain of endogluconase E1 and a transit peptide capable of transpoing the fusion protein into chloroplasts, wherein said catalytic domain of endogluconase E1 and said transit peptide are joined to form a junction site that is cleavable by a stromal processing peptidase and are separated by at least a 5 amino acid long spacer.

7. A genetic construct encoding a fusion protein comprising a catalytic domain of endogluconase E1 and an RBCA transit peptide capable of porting the fusion protein to chloroplast, wherein said catalytic domain of endogluconase E1 and said RBCA transit peptide are joined to form a junction site that is cleavable by a stromal processing peptidase (SPP), and are separated by a peptide spacer.

* * * * *

UNITED STATES PATENT AND TRADEMARK OFFICE
CERTIFICATE OF CORRECTION

PATENT NO.    : 6,429,359 B1
DATED         : August 6, 2002
INVENTOR(S)   : Gayle Lamppa It is certified that error appears in the above-identified patent and that said Letters Patent is hereby corrected as shown below:

Columns 9 and 10,
Table 2, please change "Table 2" to -- Table 1 --
Table 1, Gene Construct 3, column "Proteolytic Processing, SPP$^{1}$", please change "I" to -- $^{+}$ --
Table 1, Gene Construct 3, column "Proteolytic Processing Extr.$^{2}$", please change "I" to the minus sign -- $^{-}$ --
Table 1, Gene Construct 3, column "Transport into Isolated Chloroplasts", please change "No" to -- Yes --
Table 1, Gene Construct 5, column "Proteolytic Processing, Extr.$^{2}$", please change "++" to the minus sign -- - --
Table 1, Gene Construct 7, column "Transport into Isolated Chloroplasts", please change "N.D.*" to -- Yes --
Table 1, Gene Construct 7, column "Measure of Cellulase Activity", please change "N.D.*" to -- Yes --
Table 1, Gene Construct 8, column "Proteolytic Processing, Extr.$^{2}$", please change "++" to -- + --
Table 1, Gene Construct 9, column "Proteolytic Processing, Extr.$^{2}$", please change "++" to the minus sign -- - --
Table 1, Gene Construct 10, column "Transport into Isolated Chloroplasts", please change "Yes" to -- No --

Column 18,
Line 14, please change "transporing" to -- transporting --

Signed and Sealed this

Twenty-sixth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,429,359 B1
DATED : August 6, 2002
INVENTOR(S) : Gayle Lamppa

It is certified that error appears in the above-identified patent and that said Letters Patent is hereby corrected as shown below:

Column 17,
Line 5, please change "cihoroplasts" to -- chloroplasts --
Line 8, please delete "acid"

Signed and Sealed this

Fifth Day of October, 2004

JON W. DUDAS
*Director of the United States Patent and Trademark Office*

SEQUENCE LISTING

<160> NUMBER OF SEQ ID NOS: 12

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Peptide Motif

<400> SEQUENCE: 1

Ala Gly Gly Gly Tyr
 1               5

```
<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Fusion
      Protein Construct

<400> SEQUENCE: 2

Met Ala Gly Gly Gly Tyr Trp
 1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Fusion
      Protein Construct

<400> SEQUENCE: 3

Arg Val Thr Ala Met Ala Ala Gly Gly Gly Tyr Trp
 1               5                  10

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Fusion
      Protein Construct

<400> SEQUENCE: 4

Arg Val Thr Ala Met Ala Thr Tyr Lys Val Ala Gly Gly Gly Tyr Trp
 1               5                  10                  15

<210> SEQ ID NO 5
<211> LENGTH: 26
<212> TYPE: PRT
<213> ORGANISM: Artificial Sequence
<220> FEATURE:
<223> OTHER INFORMATION: Description of Artificial Sequence: Fusion
      Protein Construct

<400> SEQUENCE: 5

Arg Val Thr Ala Met Ala Thr Tyr Lys Val Thr Leu Ile Thr Lys Glu
 1               5                  10                  15

Ser Gly Thr Val Ala Gly Gly Gly Tyr Trp
             20                  25

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Fusion
      Protein Construct

<400> SEQUENCE: 6

Arg Val Thr Ala Met Ala Thr Tyr Lys Val Trp
 1               5                  10

<210> SEQ ID NO 7
<211> LENGTH: 16
<212> TYPE: PRT
<213> ORGANISM: Artificial Sequence
<220> FEATURE:
```

```
<223> OTHER INFORMATION: Description of Artificial Sequence: Fusion
      Protein Construct

<400> SEQUENCE: 7

Arg Val Thr Ala Met Ala Thr Tyr Lys Val Ala Gly Gly Gly Tyr Trp
 1               5                  10                  15

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Fusion
      Protein Construct

<400> SEQUENCE: 8

Arg Val Thr Ala Met Ala Ala Gly Gly Gly Tyr Trp
 1               5                  10

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Fusion
      Protein Construct

<400> SEQUENCE: 9

Arg Val Thr Ala Met Ala Thr Tyr Lys Val Ala Gly Gly Gly Tyr Trp
 1               5                  10                  15

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Fusion
      Protein Construct

<400> SEQUENCE: 10

Arg Val Thr Ala Met Ala Thr Tyr Lys Val Trp
 1               5                  10

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Fusion
      Protein Construct

<400> SEQUENCE: 11

Ser Met Thr Val Lys Ala Ala Glu Asn Glu Ala Gly Gly Gly Tyr Trp
 1               5                  10                  15

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Fusion
      Protein Construct

<400> SEQUENCE: 12

Ser Met Thr Val Lys Ala Ala Glu Asn Glu Ala Gly Gly Gly Tyr Trp
 1               5                  10                  15
```